US006764514B1

United States Patent
Li et al.

(12) United States Patent
(10) Patent No.: US 6,764,514 B1
(45) Date of Patent: Jul. 20, 2004

(54) PROSTHETIC APPARATUS AND METHOD

(75) Inventors: Lehmann K. Li, Milford, CT (US); Rhodemann Li, Greenwich, CT (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/559,899

(22) Filed: Apr. 26, 2000

Related U.S. Application Data (60) Provisional application No. 60/131,053, filed on Apr. 26, 1999.

(51) Int. Cl.[7] .................................................. A61F 2/44
(52) U.S. Cl. .................................. 623/17.12; 623/17.16
(58) Field of Search ........................... 623/17.11, 17.12, 623/17.16, 6.13, 6.59; 606/61, 99

(56) References Cited

U.S. PATENT DOCUMENTS

| | | | |
|---|---|---|---|
| 3,875,595 A | * 4/1975 | Froning | ................... 623/17.12 |
| 4,157,085 A | 6/1979 | Austad | |
| 4,828,558 A | * 5/1989 | Kelman | ..................... 623/6.13 |
| 5,005,591 A | 4/1991 | Austad | |
| 5,171,280 A | * 12/1992 | Baumgartner | ............ 623/17.12 |
| 5,534,028 A | * 7/1996 | Bao et al. | ...................... 606/61 |
| 5,562,736 A | * 10/1996 | Ray et al. | ...................... 606/61 |
| 5,674,295 A | 10/1997 | Ray et al. | |
| 5,674,296 A | 10/1997 | Bryan et al. | |
| 5,716,416 A | * 2/1998 | Lin | ......................... 623/17.16 |
| 6,132,465 A | 10/2000 | Ray et al. | |

* cited by examiner

*Primary Examiner*—Brian E Pellegrino
(74) *Attorney, Agent, or Firm*—Woodard, Emhardt, Moriarty McNett & Henry LLP (57) ABSTRACT

A prosthetic nucleus for implantation in a chamber of an intervertebral disc after removal of at least a portion of a damaged or degenerated nucleus from the chamber, comprising a wafer of biologically compatible, thin, flexible, and expandable material in a selected first configuration. The wafer is adapted to be re-shaped mechanically into a compact second configuration of cross-section sufficiently small to permit travel of the wafer through a cannula and into the disc chamber. The wafer is further adapted to substantially regain the first configuration thereof by memory upon entry into the disc chamber, and the wafer is adapted to react to an expansion-inducing agent in the disc chamber to expand to an enlarged and selected third configuration.

24 Claims, 7 Drawing Sheets

PRE-EXPANSION          POST-EXPANSION

FIG. 10

PRE-EXPANSION          POST-EXPANSION

PROSTHETIC APPARATUS AND METHOD

REFERENCE TO PENDING PRIOR PATENT APPLICATION

This patent application claims benefit of pending prior U.S. Provisional patent application Ser. No. 60/131,053, filed Apr. 26, 1999 by Lehmann K. Li for PANCAKE DISC APPARATUS AND METHOD, which patent application is hereby incorporated herein by reference.

FIELD OF THE INVENTION

This invention relates to the field of surgical devices used primarily for the repair or replacement of human tissue including, but not limited to, the nucleus pulposus of the spine. This invention further relates to the method of implanting such devices.

BACKGROUND OF THE INVENTION

The spinal column is a flexible chain of closely linked vertebral bodies. In a normal human spine there are seven cervical, twelve thoracic and five lumbar vertebral bodies. Below the lumbar vertebrae are the sacrum and coccyx. Each individual vertebra has an outer shell of hard, dense bone. Inside the vertebra is a honeycomb of cancellous bone containing red bone marrow. All of the red blood cells, and many of the white blood cells, are generated inside such cancellous bone, where the blood cells mature before being released into the blood circulation.

The spinal disc serves as a cushion between the vertebral bodies so as to permit controlled motion. A healthy disc consists of three components: a gelatinous inner core called the nucleus pulposus; a series of overlapping and laminated plies of tough fibrous rings called the annulus fibrous; and two (i.e., superior and inferior) thin cartilage layers, connecting the disc to the thin cortical bone of the adjacent vertebral bodies, called the end plates.

The spinal disc may be displaced or damaged due to trauma or disease, such as a herniation or degenerative disc disease.

A herniated disc may bulge out and compress itself onto a nerve, resulting in lower leg pain, loss of muscle control or paralysis. To treat a herniated disc, the offending nucleus portion is generally removed surgically.

Disc degeneration gradually reduces disc height, forcing the annulus to buckle, tear or separate radially or circumferentially, and causing persistent and disabling back pain. Degenerative disc disease is generally treated by surgically removing the nucleus and fusing the adjacent vertebral bodies so as to stabilize the joint.

In either case, whether removing some or all of the nucleus, these procedures ultimately place greater stress on adjacent discs to compensate for the lack of motion, which may in turn cause premature degeneration of those adjacent discs.

It has been recognized that it may be possible to replace the excised nucleus with a prosthetic implant, whereby to restore the spinal disc to its original configuration and function. Unfortunately, such implants, sometimes referred to as a prosthetic nucleus, tend to suffer from one or more deficiencies.

One deficiency of current prosthetic nuclei is that the annulus is further weakened by either large or multiple cut-outs which are required in order to insert the prosthetic nucleus into the interior of the spinal disc. Additionally, any flaps or cut-outs of the annulus are not easily repaired; thus, there may be a concern that the prosthetic nucleus may eventually work its way back out of the disc space. A further deficiency of current, less-invasive prosthetic nuclei (see, for example, U.S. Pat. No. 5,674,295, issued Oct. 7, 1997 to Ray et al.) is that multiple, laterally-spaced implants typically have to be used, which suggests that the side-by-side positioning of the several implants has to be carefully considered so as to ensure proper load carrying.

Modern trends in surgery include the restoration of bodily function and form (i.e., the repair) of anatomical structures through the use of minimally invasive surgical techniques. The ability to surgically repair damaged tissues or joints, creating as few and as small incisions as possible, generally produces less trauma, less pain and better clinical outcomes for the patient.

OBJECTS OF THE INVENTION

It is, therefore, one object of the present invention to provide an apparatus and minimally invasive method for delivering material into human tissue.

Another object of the present invention is to provide an apparatus and method for delivering an implant into the inner portion of a damaged intervertebral disc for restoration of the disc. The implant is inserted through a small opening in the annulus of the disc so as to replace the natural nucleus pulposus of the disc.

SUMMARY OF THE INVENTION

These and other objects are addressed by the present invention.

More particularly, one feature of the present invention is the provision of an apparatus and method for delivering a small, flexible implant which expands in biologic tissue. The apparatus and method for delivering the small, flexible implant into biologic tissue comprises the following steps:

(a) accessing and preparing the intended insertion space;

(b) inserting into the space, through a cannula or otherwise, the small flexible implant that is expandable through memory, hydration or otherwise; and (c) after insertion into the space, the small flexible implant expands so as to form a second shape which is larger than the shape of the implant during insertion.

Steps (a) through (c) may be performed through open or minimally invasive surgical techniques.

Another feature of the present invention is the provision of a prosthetic nucleus for implantation in a chamber of an intervertebral disc after removal of at least a portion of a damaged or degenerated nucleus from the chamber. The prosthetic nucleus comprises a wafer of biologically compatible, thin, flexible, and expandable material in a selected first configuration, the wafer being adapted to be re-shaped mechanically into a compact second configuration of cross-section sufficiently small to permit travel of the wafer through a cannula and into the disc chamber, the wafer being adapted to substantially regain the first configuration thereof by memory upon entry into the disc chamber, and the wafer being adapted to react to an expansion-inducing agent in the disc chamber to expand to an enlarged and selected third configuration.

In accordance with a further feature of the present invention, there is provided a prosthetic nucleus for implantation in a chamber of an intervertebral disc after removal of at least a portion of a damaged or degenerated nucleus from the chamber. The prosthetic nucleus comprises a wafer of biologically compatible and expandable material in a selected first configuration. The wafer is adapted to be collapsed into a compact second configuration of cross-section sufficiently small to permit travel of the wafer through a cannula and into the disc chamber, and the wafer is adapted to react to an expansion-inducing agent in the disc chamber to expand to an enlarged and selected third configuration.

In accordance with a further feature of the present invention, there is provided a prosthetic nucleus for implantation in a chamber of an intervertebral disc after removal of at least a portion of a damaged or degenerated nucleus from the chamber. The prosthetic nucleus comprises a wafer of biologically compatible, thin, flexible, and expandable material in a selected first configuration. The wafer is adapted to be re-shaped mechanically into a compact second configuration of cross-section sufficiently small to permit travel of the wafer through a cannula and into the disc chamber. The wafer is adapted to substantially regain the first configuration thereof by memory upon entry into the disc chamber, and the wafer is adapted to react to an expansion-inducing agent introduced into the wafer to expand to an enlarged and selected third configuration.

In accordance with a still further feature of the present invention, there is provided a prosthetic nucleus for implantation in a chamber of an intervertebral disc after removal of at least a portion of a damaged or degenerated nucleus from the chamber. The prosthetic nucleus comprises a plurality of wafers of biologically compatible and expandable material, each in a selected first configuration. The wafers are adapted to be re-shaped mechanically into a compact second configuration of cross-section sufficiently small to permit travel of the wafers through a cannula and into the disc chamber. The wafers are adapted to substantially regain the first configuration thereof by memory upon entry into the disc chamber, and are adapted to react to an expansion-inducing agent to expand to an enlarged and selected third configuration.

BRIEF DESCRIPTION OF THE DRAWINGS

These and other objects and features of the present invention will be further disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
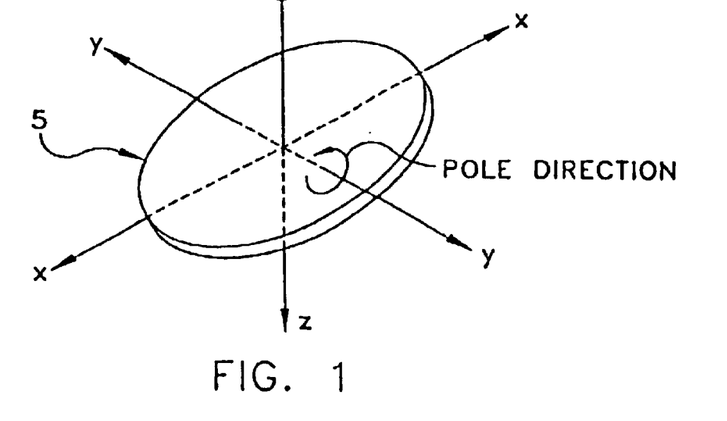
FIG. 1 is a schematic diagram showing an implant formed in accordance with the present invention.

Looking first at FIG. 1, there is shown an implant 5 which may function as a prosthetic nucleus or other prosthetic tissue-replacing device. For convenience, implant 5 will hereinafter generally be discussed in the context of a prosthetic nucleus for a damaged or diseased spinal disc; however, it should be appreciated that implant 5 may also be used to replace other biologic tissue as well.

Implant 5 generally comprises a wafer of biologically-compatible, thin, flexible and expandable material in a selected first configuration, e.g., a disc or pancake shape such as shown in FIG. 1. Implant 5 is adapted to be re-shaped mechanically into a compact second configuration of cross-section sufficiently small to permit minimally-invasive insertion into the chamber of a spinal disc (or other tissue) and is adapted to substantially regain its aforementioned first configuration by memory upon positioning in the disc chamber. In addition, implant 5 is also adapted to react to an expansion-inducing agent when seated in the disc chamber so as to expand to an enlarged and selected third configuration.

Figure 2:
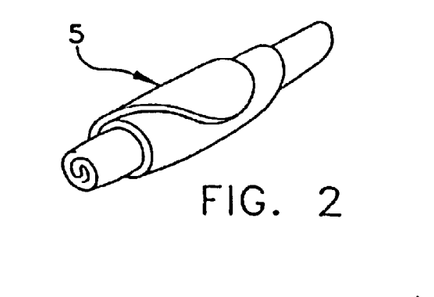
FIG. 2 is a schematic diagram showing the implant of FIG. 1 rolled into a cigar-like shape.
Figure 3:
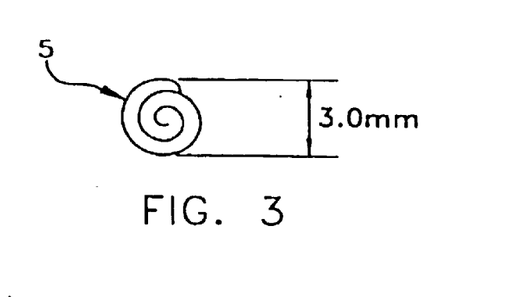
FIG. 3 is another schematic diagram showing the same implant rolled into a cigar-like shape.
Figure 4:
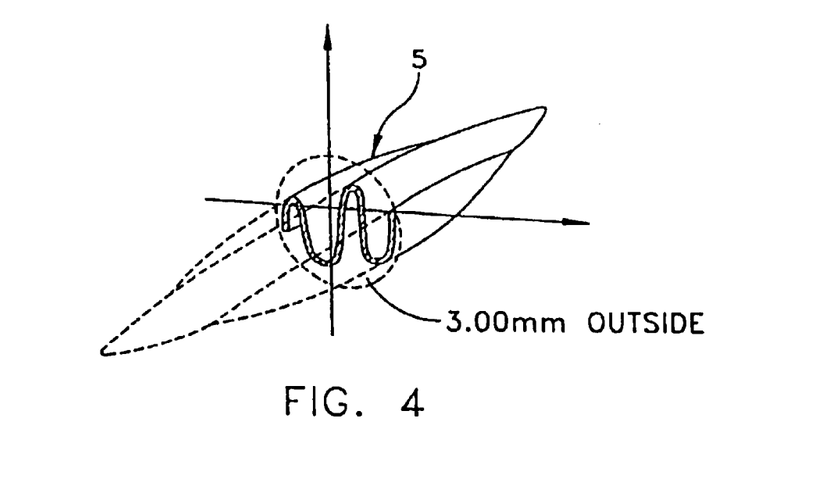
FIG. 4 is a schematic diagram showing the implant of FIG. 1 curled or folded into a bellows-like shape.
Figure 5:
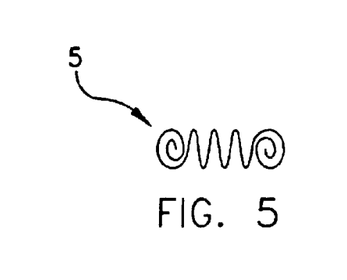
FIG. 5 is a schematic diagram showing the implant of FIG. 1 both rolled and curled or folded so as to assume a more compact configuration.

More particularly, implant 5 is constructed so that it may be rolled, such as in the manner shown in FIGS. 2 and 3, so as to resemble a cigar, whereby to allow for easy insertion into a cavity via a small opening. Alternatively, implant 5 may be curled or folded, e.g., in the manner of a bellows, such as is shown in FIG. 4, whereby to allow for easy insertion into a cavity through a small opening. Or implant 5 may be both rolled and curled or folded, such as is shown in FIG. 5, so as to allow for easy insertion into a cavity through a small opening.

Figure 6:
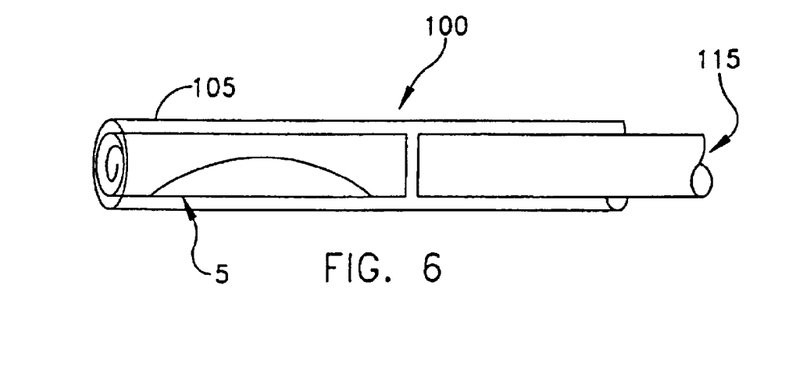
FIG. 6 is a schematic diagram showing the implant of FIG. 2 loaded into a cannula.

Once rolled, curled and/or folded, implant 5 may be inserted into a delivery cannula 100, such as is shown in FIG. 6. If desired, implant 5 may be inserted into delivery cannula 100 at the time of use; alternatively, implant 5 may be inserted into delivery cannula 100 during manufacture.

Figure 7:
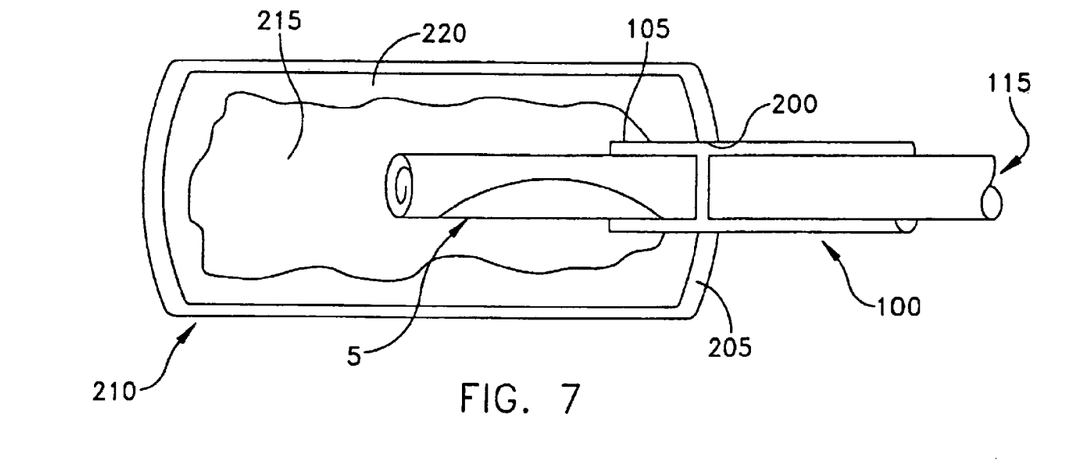
FIG. 7 is a schematic diagram showing the cannula delivering the implant to a chamber formed in tissue.

Looking next at FIG. 7, the distal end 105 of cannula 100 may thereafter be moved through a small opening 200 formed in the annulus 205 of a spinal disc 210, so that the distal end of the cannula is positioned in a hollowed-out cavity 215 formed in the nucleus pulposus 220. Implant 5 may then be ejected into place using the cannula's associated plunger 115.

Figure 8:
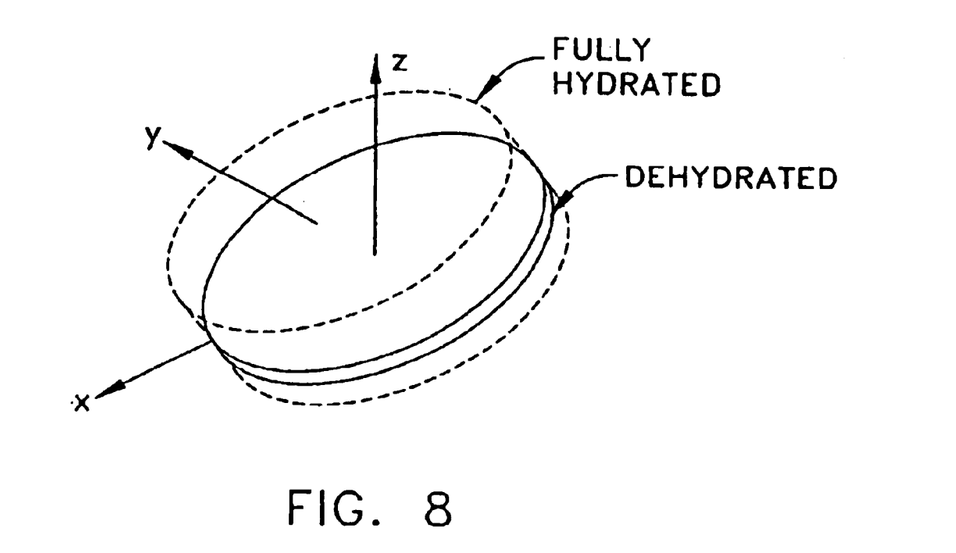
FIG. 8 is a schematic diagram illustrating the implant of FIG. 1 expanding.
Figure 9:
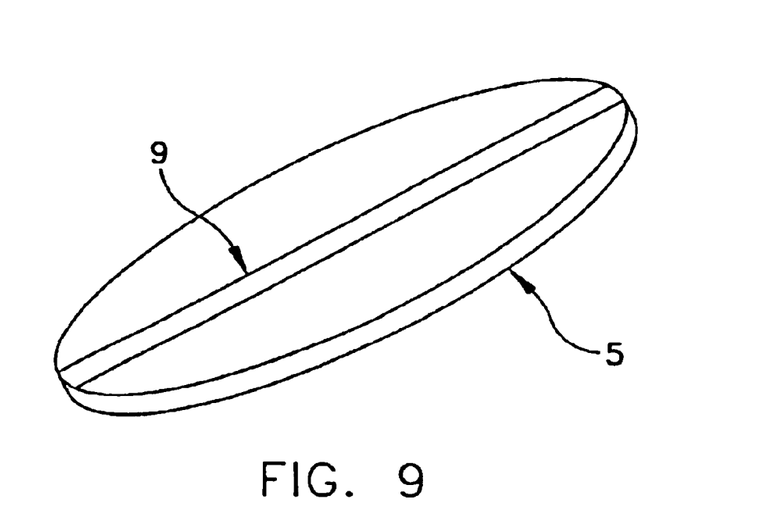
FIG. 9 is a schematic diagram illustrating an alternative form of implant.

Once inserted in the biological tissue, flexible implant 5 may expand in the x or y direction (FIG. 8), by unrolling or uncurling or unfolding by memory. If desired, components such as superelastic struts may be added to implant 5 so as to assist in the unrolling or uncurling or unfolding. See, for example, FIG. 9, where a superelastic strut 7 is shown on implant 5. In the event that flexible implant 5 encounters any stray tissue within hollowed-out cavity 215 while unrolling or uncurling or unfolding, a tool may be inserted into the cavity to assist complete deployment of the implant.

Once implant 5 is positioned in the disc chamber, it may thereafter expand in the z direction (FIG. 8) through reaction to an expansion-inducing agent. By way of example but not limitation, implant 5 may be formed out of a dehydrated hydrogel, and expansion in the z direction may occur through re-hydration. Alternatively, expansion in the z direction could be achieved by forming implant 5 of a different sort of material, e.g., a temperature sensitive material, and the expansion-inducing agent could comprise natural body heat or externally-supplied heat. Or implant 5 could be formed out of a chemically reactive material and the expansion-inducing agent could be a biologically compatible chemical delivered to the site by a syringe or the like.

Figure 10:
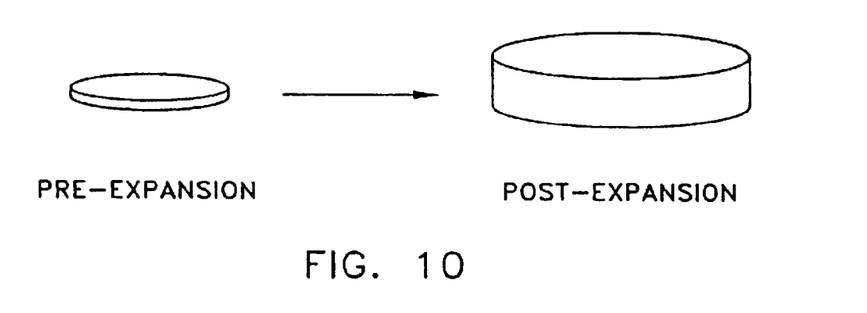
FIGS. 10–13 are schematic diagrams illustrating expansion of the implant from an aforementioned first configuration to an aforementioned third configuration.

It should also be appreciated that implant 5 may expand in more than just the z direction through reaction to the expansion-inducing agent. By way of example but not limitation, and looking now at FIG. 10, implant 5 may expand in the x, y and z directions through reaction to the expansion-inducing agent.

Furthermore, with respect to the final expansion of implant 5 within the tissue cavity (i.e., the expansion of implant 5 to its aforementioned "third configuration"), implant 5 may be formed so that it expands equally in all directions, or it may be formed so that it expands differently in different directions.

By way of example but not limitation, as alluded to above, implant 5 can be formed so that the expansion to its aforementioned third configuration occurs only in the z direction, and not at all in the x and y directions. This configuration can be very useful in a prosthetic nucleus application, where it is generally desirable to provide vertical support without imposing lateral pressure on the annulus.

Figure 11:
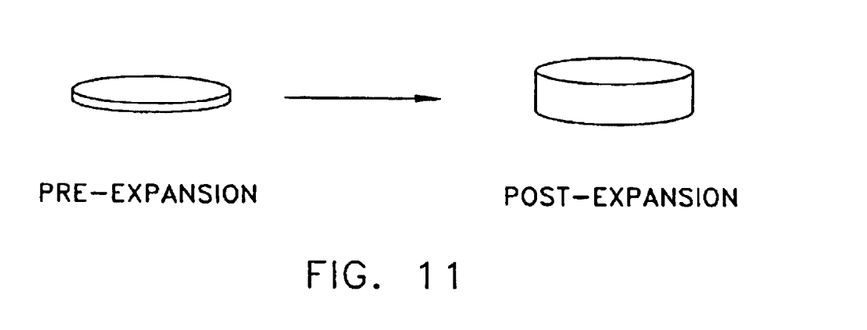

Alternatively, implant 5 can be formed so that the expansion to its aforementioned third configuration occurs primarily in the z direction, and relatively little in the x and y directions. See, for example, FIG. 11, where the expansion of implant 5 to its aforementioned third configuration occurs primarily in the z direction, and relatively little in the x and y directions.

Figure 12:
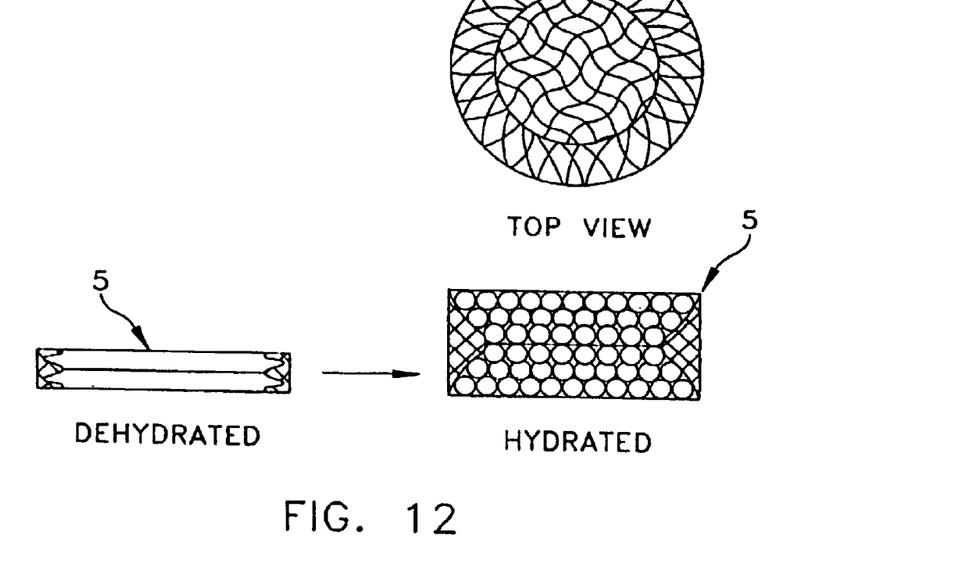

If desired, implant 5 can be constructed with a composite construction, utilizing two or more different materials, such as is shown in FIG. 12, so as to yield the desired expansion properties. And implants 5 may have multiple internal and/or external surfaces (e.g., walls, barriers, supports, etc.) that may be connected and/or reinforced and/or made more rigid so as to encourage or to direct expansion in a desired manner.

Figure 13:
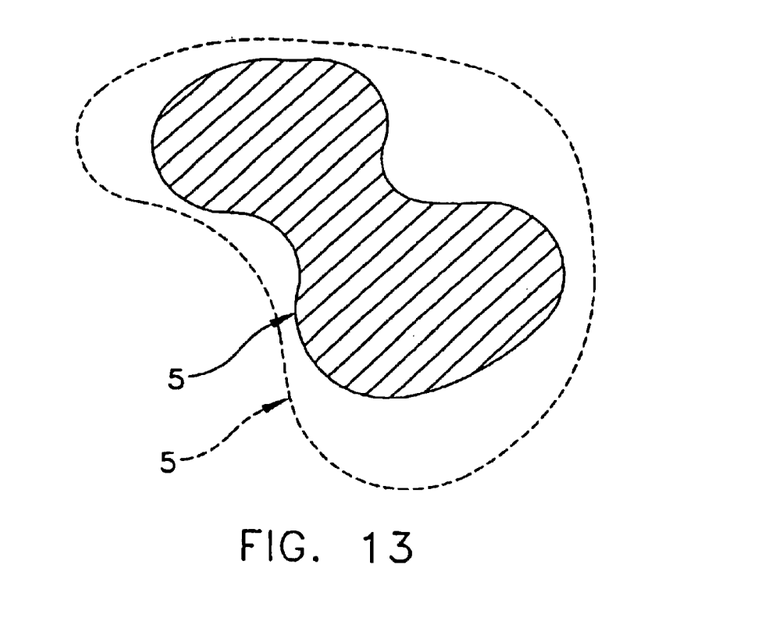

By way of further example but not limitation, see also FIG. 13, where implant 5 expands differently in different directions, i.e., so that the peripheral geometry of the implant actually changes.

Regardless of the particular construction utilized, implant 5 is preferably formed out of a flexible and expandable material which (i) has a selected first configuration; (ii) can be reshaped mechanically into a more compact second configuration so as to permit easy insertion into an internal cavity, (iii) will thereafter return by memory to its aforementioned first configuration, and (iv) will then expand to an enlarged third configuration.

It will, of course, be appreciated that implant 5 will be formed out of one or more materials consistent with its function. For example, where implant 5 is to be used as a prosthetic nucleus for a spinal disc, implant 5 will be formed out of a material which can appropriately accommodate the anatomical loads imposed on the disc. For example, where implant 5 is to be used as a prosthetic nucleus, implant 5 may be formed out of a hydrogel. Such a material can be advantageous in a prosthetic nucleus application, due to its ability to be dehydrated and re-hydrated, and due to its ability to dynamically release and re-absorb water in response to compressive loads whereby to function as a sort of shock absorber.

Figure 14:
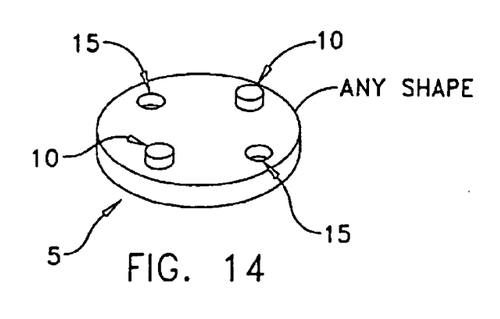
FIGS. 14 and 15 are schematic diagrams illustrating one technique for interlocking two implants formed in accordance with the present invention.
Figure 15:
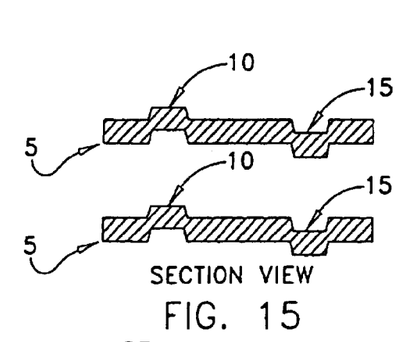
Figure 16:
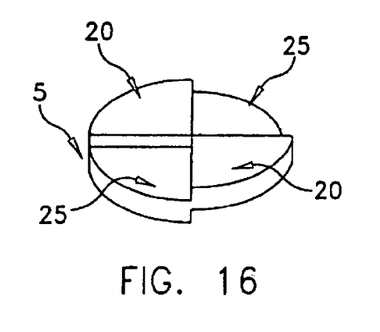
FIGS. 16–18 are schematic diagrams illustrating another technique for interlocking two implants formed in accordance with the present invention.
Figure 17:
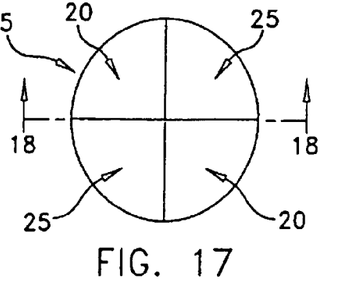
Figure 18:
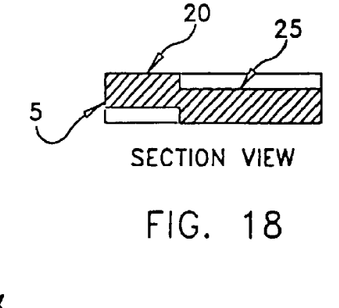
Figure 19:
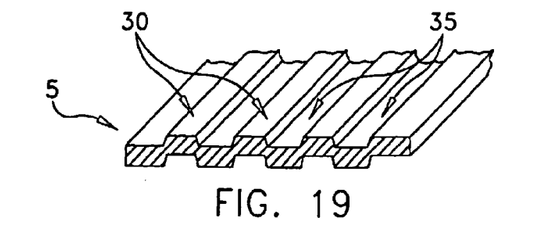
FIG. 19 is a schematic diagram illustrating yet another technique for interlocking two implants formed in accordance with the present invention.

In some cases a single implant 5 may be adequate to restore proper function to the tissue. However, in other cases it may be desirable to stack two or more implants vertically to restore proper function to the tissue. In this case, where multiple implants 5 are to be placed in the biological tissue, it may be desirable to have means to align or orient the members in a certain way. This orientation can be achieved by having alternating patterns ingrained into implants 5 such that they interlock together. The interlocking can be accomplished using pegs 10 and recesses 15 (FIGS. 14 and 15), or projections 20 and recesses 25, (FIGS. 16–18), or ribs 30 and recesses 35 (FIG. 19), etc. Alternatively, implants 5 may be chemically bonded (e.g., glued) to one another.

Modifications of the Preferred Embodiments

Implant 5 may be shaped as a circular disc, oval, kidney, polygon, any symmetrical or asymmetrical geometrical figure, or as a solid or with fenestrations. Implant 5 may be trimmed or shaped at the time of use so as to accommodate unique cavity dimensions.

Implant 5 may have biocompatible components such as, but not limited to, cells, genes, chemicals, particles, metals, etc. to serve various purposes.

Figure 20:
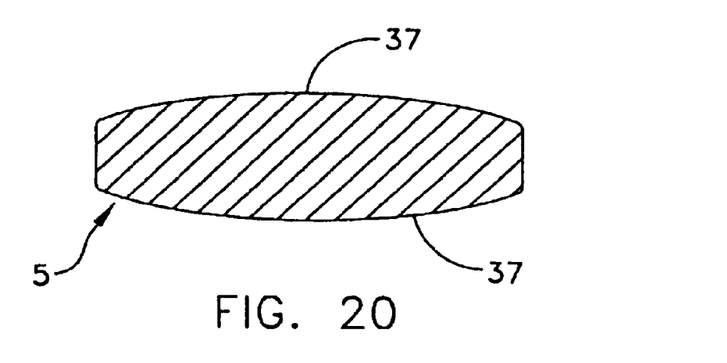
FIGS. 20–22 are schematic diagrams illustrating other alternative forms of implants.

The amount of lateral curvature of implant 5 can be varied such that when expanded, the height of one section of the implant can be different from another section, for example, the middle could be taller than the outer portion of the implant so as to compensate for the concave vertebral end plates. See, for example, FIG. 20, where an implant 5 has convex upper and lower surfaces 37.

Figure 21:
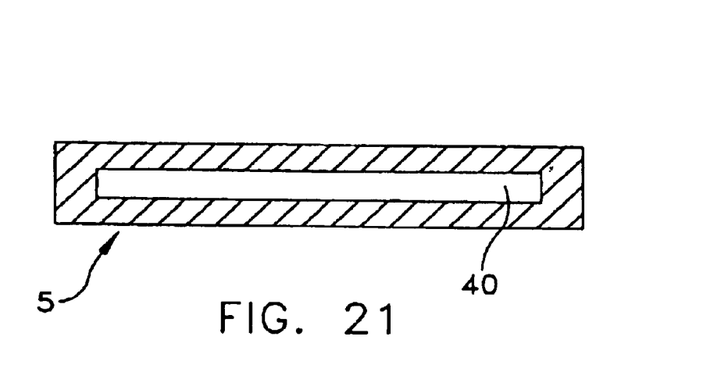
Figure 22:
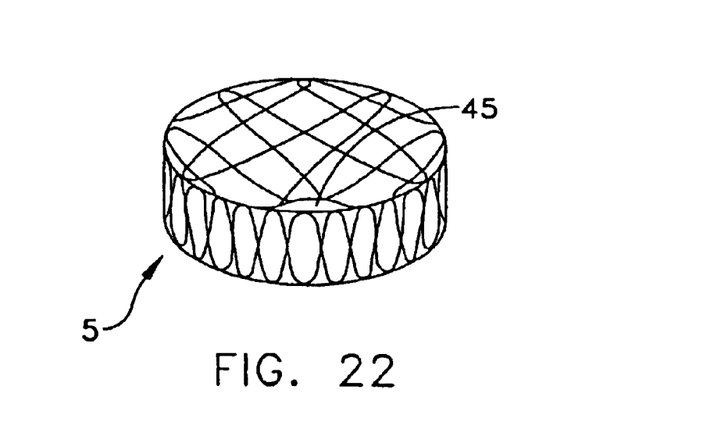

Implant 5 may also include an internal opening or chamber if desired. See, for example, FIG. 21, where an implant 5 includes an internal chamber 40, and FIG. 22, where an implant 5 includes a central opening 45.

Implant 5 may be encased in another flexible member. The latter member may be of a flexible weave pattern, or of a material which permits, assists or directs the implant to act in certain defined ways or directions, whether by flow, hydration, swelling, curing or otherwise.

Advantages of the Invention

A principal advantage of the present invention is that only a small insertion port (e.g., less than 5 mm in diameter) is required to implant the flexible implant, thus minimizing the trauma to the annulus or other peripheral tissue. As an expanding flexible implant (or series of implants) fills up the intended insertion site, lateral stability is achieved because the member(s) assume(s) a volumetric load-carrying area.

Another advantage of utilizing a flexible implant is that a series of implants can be easily stacked or positioned so as to accommodate varying insertion site dimensions.

Also, the flexible implants can be customized prior to insertion by trimming, or shaping, so as to accommodate unique insertion site dimensions.

What is claimed is:

1. A prosthetic intervertebral nucleus for implantation in a chamber of an intervertebral disc after removal of at least a portion of a damaged or degenerated nucleus from the chamber, the prosthetic nucleus comprising:

a wafer of biologically compatible, thin, flexible, and expandable material having a first substantially planar structural configuration defining a first thickness substantially less than a height of the disc chamber;

said wafer having a second non-planar mechanically re-shaped structural configuration defining a cross-section sufficiently small to permit travel of said wafer through a cannula and into the disc chamber;

said wafer substantially regaining the first structural configuration thereof by memory upon entry into the disc chamber; and said wafer having a third expanded structural configuration formed by a reaction to an expansion-inducing agent in the disc chamber, said third structural configuration defining a second thickness approximately equal to the height of the disc chamber.

2. A prosthetic nucleus in accordance with claim 1 wherein the first configuration of said wafer is at least one of circular, annular, oval, kidney, polygonal, symmetrical, and asymmetrical.

3. A prosthetic nucleus in accordance with claim 1 wherein the expansion-inducing agent comprises a selected one of temperature in the chamber; a substance in the chamber; and a substance introduced into the nucleus in the chamber.

4. A prosthetic nucleus in accordance with claim 3 wherein the expansion-inducing substance comprises a fluid.

5. A prosthetic nucleus in accordance with claim 4 wherein the fluid is water.

6. A prosthetic nucleus in accordance with claim 4 wherein said wafer, in the third configuration, exhibits elastic properties providing the disc with shock-absorber capabilities.

7. A prosthetic nucleus in accordance with claim 1 wherein said wafer is provided with fenestrations.

8. A prosthetic nucleus in accordance with claim 1 wherein said wafer is adapted to expand in a selected direction so as to assume the third configuration.

9. A prosthetic nucleus in accordance with claim 1 wherein said wafer is provided with at least one additional component to facilitate return of said wafer from said second configuration to said first configuration for stability and strength.

10. A prosthetic nucleus in accordance with claim 1 wherein said wafer is provided with an internal chamber.

11. A prosthetic intervertebral nucleus for implantation in a chamber of an intervertebral disc after removal of at least a portion of a damaged or degenerated nucleus from the chamber, the prosthetic nucleus comprising:

a wafer of biologically compatible, thin, flexible, and expandable material having a first substantially planar structural configuration;

said wafer having a second non-planar mechanically re-shaped structural configuration defining a cross-section sufficiently small to permit travel of said wafer through a cannula and into the disc chamber, said second non-planar structural configuration comprising at least one of a rolled, curled and folded configuration;

said wafer substantially regaining the first structural configuration thereof by memory upon entry into the disc chamber; and said wafer having a third expanded structural configuration formed by a reaction to an expansion-inducing agent in the disc chamber.

12. A prosthetic nucleus in accordance with claim 11 wherein said wafer regains the first configuration by one of unrolling, uncurling and unfolding.

13. A prosthetic intervertebral nucleus for implantation in a chamber of an intervertebral disc after removal of at least a portion of a damaged or degenerated nucleus from the chamber, the prosthetic nucleus comprising:

a wafer of biologically compatible, thin, flexible, and expandable material having a first substantially planar structural configuration defining a first thickness substantially less than a height of the disc chamber;

said wafer having a second non-planar collapsed structural configuration defining a cross-section sufficiently small to permit travel of said wafer through a cannula and into the disc chamber; and said wafer having a third expanded structural configuration formed by a reaction to an expansion-inducing agent in the disc chamber, said third structural configuration defining a second thickness approximately equal to the height of the disc chamber.

14. A prosthetic intervertebral nucleus for implantation in a chamber of an intervertebral disc after removal of at least a portion of a damaged or degenerated nucleus from the chamber, the prosthetic nucleus comprising:

a wafer of biologically compatible, thin, flexible, and expandable material having a first substantially planar structural configuration;

said wafer having a second non-planar collapsed structural configuration defining a cross-section sufficiently small to permit travel of said wafer through a cannula and into the disc chamber, said second non-planar structural configuration comprising at least one of a rolled, curled and folded configuration; and said wafer having a third expanded structural configuration formed by a reaction to an expansion-inducing agent in the disc chamber.

15. A prosthetic intervertebral nucleus for implantation into a chamber of an intervertebral disc after removal of at least a portion of a damaged or degenerated nucleus, the prosthetic nucleus comprising: an implant having a first substantially planar structural configuration, said implant having a second non-planar collapsed structural configuration for insertion into the disc chamber, said second non-planar structural configuration comprising a rolled configuration, said implant substantially regaining said first substantially planar structural configuration by memory upon entry into the disc chamber said implant having a third expanded structural configuration formed by a reaction to an expansion-inducing agent within the disc chamber.

16. The prosthetic nucleus in accordance with claim 15 wherein said implant is inserted through a cannula while in said second configuration and into the disc chamber.

17. A prosthetic intervertebral nucleus for implantation into a chamber of an intervertebral disc after removal of at least a portion of a damaged or degenerated nucleus, the prosthetic nucleus comprising:

an implant having a first substantially planar structural configuration, said implant having a second non-planar collapsed structural configuration for insertion into the disc chamber, said second non-planar structural configuration comprising a rolled configuration, said implant substantially regaining said first substantially planar structural configuration by memory upon entry into the disc chamber, said implant comprising a wafer of biologically compatible, thin, flexible and expandable material.

18. A prosthetic intervertebral nucleus for implantation into a chamber of an intervertebral disc after removal of at least a portion of a damaged or degenerated nucleus, the prosthetic nucleus comprising:

an implant having a first substantially planar structural configuration, said implant having a second non-planar collapsed structural configuration for insertion into the disc chamber, said second non-planar structural configuration comprising a curled configuration, said implant substantially regaining said first substantially planar structural configuration by memory upon entry into the disc chamber, said implant having a third expanded structural configuration formed by a reaction to an expansion-inducing agent within the disc chamber.

19. The prosthetic nucleus in accordance with claim 18 wherein said implant is inserted through a cannula while in said second configuration and into the disc chamber.

20. A prosthetic intervertebral nucleus for implantation into a chamber of an intervertebral disc after removal of at least a portion of a damaged or degenerated nucleus, the prosthetic nucleus comprising:

an implant having a first substantially planar structural configuration, said implant having a second non-planar collapsed structural configuration for insertion into the disc chamber, said second non-planar structural configuration comprising a curled configuration, said implant substantially regaining said first substantially planar structural configuration by memory upon entry into the disc chamber, said implant comprising a wafer of biologically compatible, thin, flexible and expandable material.

21. A prosthetic intervertebral nucleus for implantation into a chamber of an intervertebral disc after removal of at least a portion of a damaged or degenerated nucleus, the prosthetic nucleus comprising:

an implant having a first substantially planar structural configuration, said implant having a second non-planar collapsed structural configuration for insertion into the disc chamber, said second non-planar structural configuration comprising a folded configuration, said implant substantially regaining said first substantially planar structural configuration by memory upon entry into the disc chamber, said implant having a third expanded structural configuration formed by a reaction to an expansion-inducing agent within the disc chamber.

22. The prosthetic nucleus in accordance with claim 21 wherein said implant is inserted through a cannula while in said second configuration and into the disc chamber.

23. A prosthetic intervertebral nucleus for implantation into a chamber of an intervertebral disc after removal of at least a portion of a damaged or degenerated nucleus, the prosthetic nucleus comprising:

an implant having a first substantially planar structural configuration, said implant having a second non-planar collapsed structural configuration for insertion into the disc chamber, said second non-planar structural configuration comprising a folded configuration, said implant substantially regaining said first substantially planar structural configuration by memory upon entry into the disc chamber, said implant comprising a wafer of biologically compatible, thin, flexible and expandable material.

24. The prosthetic nucleus in accordance with claim 23 wherein said implant has a third expanded structural configuration formed by a reaction to an expansion-inducing agent within the disc chamber.

\* \* \* \* \*